United States Patent [19]
Duncan

[11] Patent Number: 6,041,642
[45] Date of Patent: Mar. 28, 2000

[54] METHOD AND APPARATUS FOR SENSING THE NATURAL FREQUENCY OF A CANTILEVERED BODY

[75] Inventor: Michael G. Duncan, Clinton, Tenn.

[73] Assignee: Lockheed Martin Energy Systems, Inc., Oak Ridge, Tenn.

[21] Appl. No.: 09/090,365

[22] Filed: Jun. 4, 1998

[51] Int. Cl.[7] .................................................. G01N 27/00
[52] U.S. Cl. .......................... 73/24.01; 73/24.06; 73/579; 422/88
[58] Field of Search .............................. 73/579, 597, 629, 73/24.01, 24.02, 24.03, 24.04, 24.05, 24.06, 31.01, 31.02, 31.03, 31.04, 31.05; 422/83, 88

[56] References Cited

U.S. PATENT DOCUMENTS

| | | | |
|---|---|---|---|
| 3,726,129 | 4/1973 | Thorne | 73/67.2 |
| 3,828,607 | 8/1974 | Janzen et al. | 73/23 |
| 3,889,525 | 6/1975 | Bailey | 73/658 |
| 4,014,208 | 3/1977 | Moore et al. | 73/629 |
| 4,363,242 | 12/1982 | Heyman | 73/579 |
| 4,368,438 | 1/1983 | Stienstra | 331/14 |
| 4,385,516 | 5/1983 | Uffelman | 73/24 |
| 4,470,121 | 9/1984 | Ebert | 73/579 |
| 4,817,430 | 4/1989 | Benes et al. | 73/579 |
| 4,912,978 | 4/1990 | Solmos | 73/579 |
| 5,214,955 | 6/1993 | Yost et al. | 73/24.05 |
| 5,445,008 | 8/1995 | Wachter et al. | 73/24.06 |
| 5,719,324 | 2/1998 | Thundat et al. | 73/24.01 |

*Primary Examiner*—Hezron Williams
*Assistant Examiner*—Helen C. Kwok
*Attorney, Agent, or Firm*—Quarles & Brady LLP

[57] ABSTRACT

A method and apparatus for measuring the natural resonant frequency of a spring element by monitoring a phase difference between an output signal from the spring element and an input signal to the spring element and by adjusting frequency of the input signal until a detected phase difference signals that the natural resonant frequency has been reached. The method and apparatus are applied to a micro-cantilevered elements used to measure gas compositions and concentrations. Such elements are provided with coatings that absorb gas to cause deflections and changes in the mass or spring constant of the cantilevered element. These changes correspond to changes in the natural resonant frequency of the cantilevered element which are measured using the method and apparatus described herein.

11 Claims, 3 Drawing Sheets

METHOD AND APPARATUS FOR SENSING THE NATURAL FREQUENCY OF A CANTILEVERED BODY

STATEMENT REGARDING FEDERALLY SPONSORED RESEARCH

This invention was made with Government support under Contract No. DE-AC05-84OR21400 awarded by the U.S. Dept. of Energy. The Government has certain rights in the invention.

TECHNICAL FIELD

The field of the invention is methods and apparatus for detecting the natural frequency of cantilever deflection in response to natural phenomena, such as absorption of a gas.

DESCRIPTION OF THE BACKGROUND ART

Micro-cantilever sensors are being developed to measure gas composition, concentrations, humidity, pressure and other parameters. Such sensor elements may be provided with a coating which will absorb the gas, causing the sensor to deflect and to change its mass or spring constant in such deflection. An accurate way of measuring such deflection is through measurement of the cantilever's natural resonant frequency. Changes in mass or spring constant cause a change in this natural resonant frequency which can be measured with a high degree of accuracy and sensitivity.

There has not been, however, a low-cost, automatic method of measuring the natural resonant frequency of a micro-cantilevered body. Such bodies are typically fabricated in a monolithic structure resembling an integrated circuit chip. One possible technique involves manually tuning an oscillator and looking for a peak amplitude with a lock-in amplifier. One drawback of this method is a frequency offset error that depends upon the Q of the cantilever. Another drawback is that this type of amplifier is deemed to be too expensive. Another possible technique would utilize Fast Fourier Transform (FFT) computation to find the peak amplitude.

SUMMARY OF THE INVENTION

The present invention measures the natural frequency of a spring element by detecting a phase difference between one signal produced by the spring element and a second signal, which represents the signal that is applied to cause the spring element to vibrate, but which is also applied directly to a phase detector. In this way, the phase difference is the result of the movement of the spring element. The frequency of the signal applied to the spring element is then automatically adjusted to reach a predetermined phase difference which is known to result from deflection of the spring element at the natural resonant frequency.

The invention makes use a voltage controlled oscillator (VCO) circuit which provides the signal to the spring element and the signal that is applied directly to the phase detector. This is in contrast to the conventional use of voltage controlled oscillators in phase locked loops, in which the VCO output signal is adjusted to maintain a preset phase difference relative to an input signal from another source.

While the invention is described here in terms of a microcantilever and other discrete circuitry, the invention could be manufactured as an individual integrated circuit, while still incorporating the features disclosed herein. Also, the invention can be practiced with control functions being executed by a computer program.

The invention provides a control circuit with very fast response or lock-in time and very short settling time. The invention provides a control circuit with high noise immunity and a frequency lock range that is unaffected by noise bandwidth.

Other objects and advantages, besides those discussed above, will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention, and, therefore, reference is made to the following claims which follow the description for determining the scope of the invention.

DETAILED DESCRIPTION OF THE PREFERRED EMBODIMENT

Figure 1:
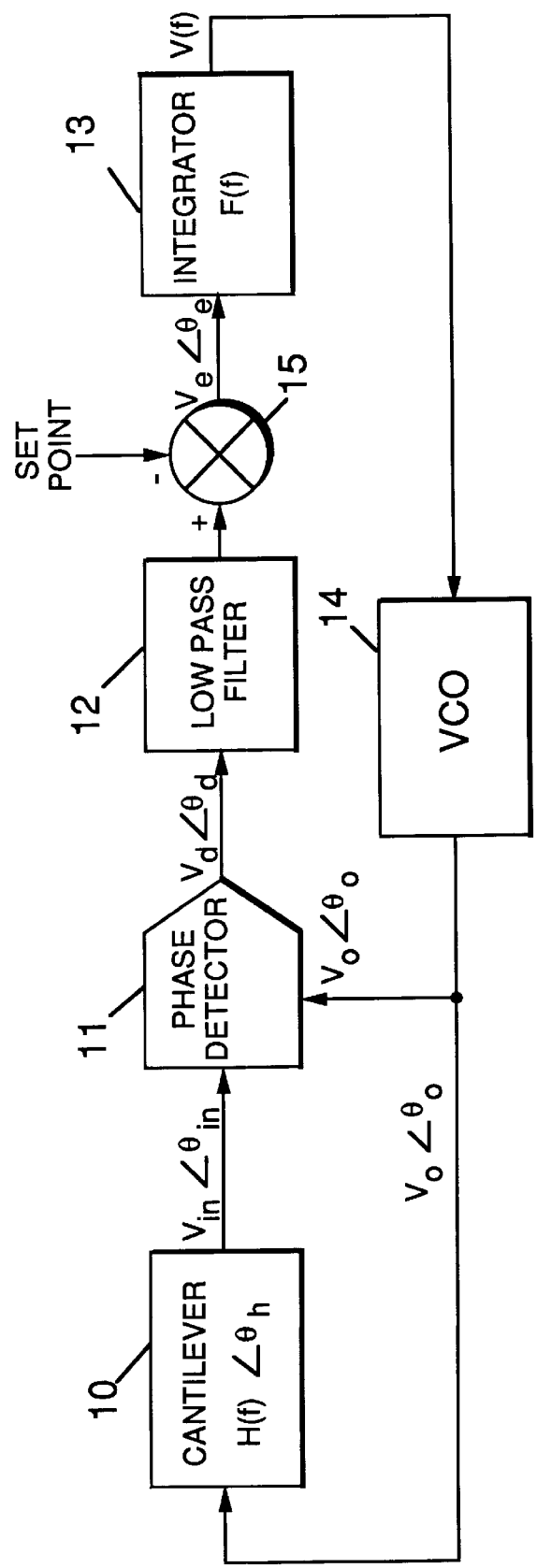
FIG. 1 is a block diagram of a method for carrying out the present invention.

Referring to FIG. 1, the invention is incorporated in a method and circuit for sensing the natural frequency of a cantilevered spring element. As seen in FIG. 1, a voltage controlled oscillator (VCO) circuit 14 generates an AC signal having a magnitude, $V_o$, and a phase, $\theta_o$, which is an excitation input signal to a cantilevered element 10. The cantilevered element 10 has a transfer function with a magnitude, $|H(f)|$, and a phase, $\theta_h$.

If the VCO phase is $\theta_o$ and the cantilever phase is $\theta_h$, then the cantilever output phase is $$\theta_{in} = \theta_o + \theta_h.$$

Figure 2:
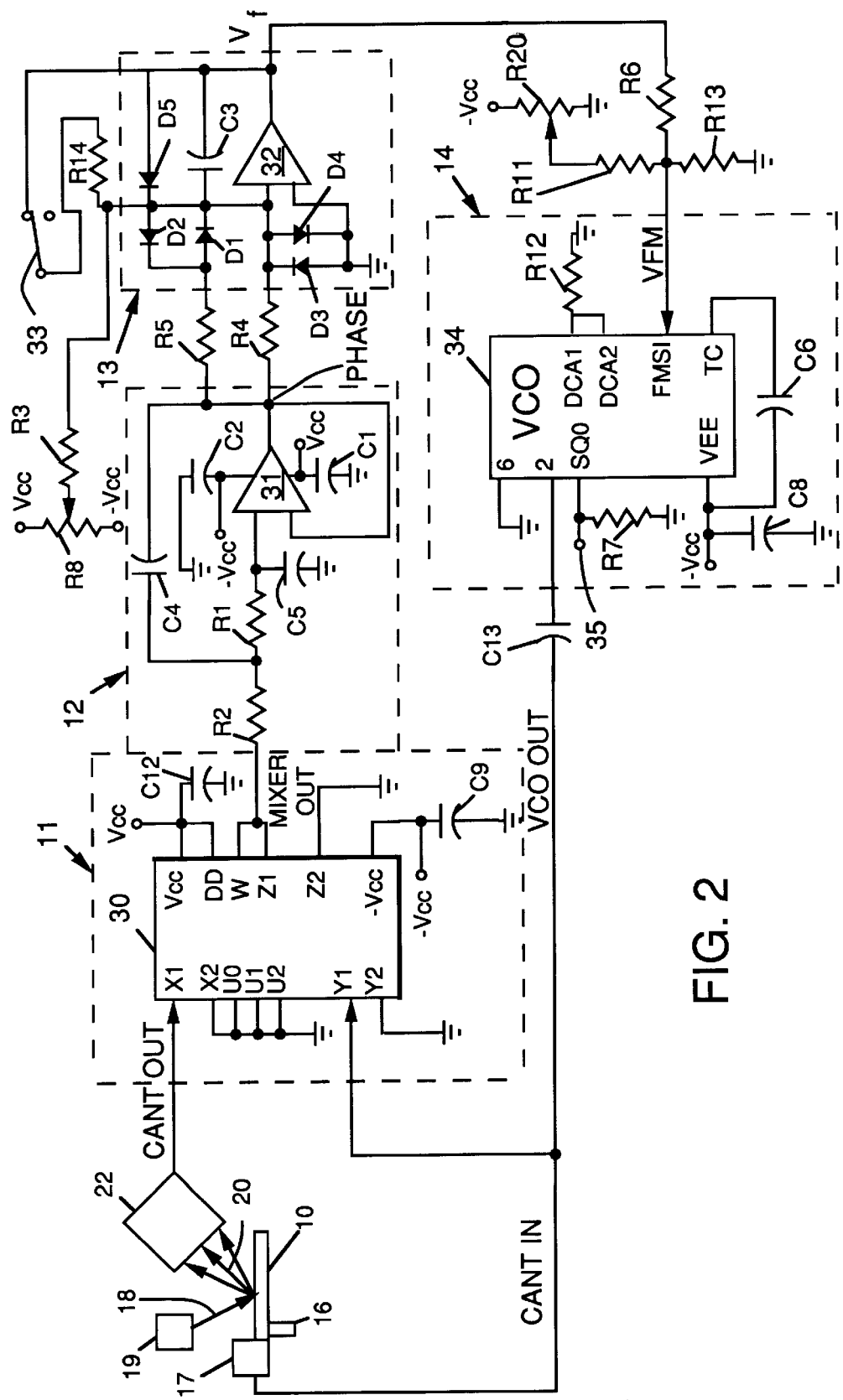
FIG. 2 is a detailed schematic view of a apparatus for carrying out the method of FIG. 1.

The cantilever output signal which has a magnitude, $V_{in}$, and a phase, $\theta_{in}$, becomes an input signal to a phase detector circuit 11. The phase detector circuit 11 also receives a signal having the magnitude, $V_o$, and the phase, $\theta_o$, directly from the voltage controlled oscillator (VCO) circuit 14. The phase detector output, $V_d$, is proportional to the phase shift of the cantilever at the VCO frequency ($f_o$) as shown in FIG. 2. The phase detector output is $$V_d = k_d(\theta_{in} - \theta_o) = k_d \theta_h,$$

where $k_d$ is the phase detector gain. Thus, the detected phase ($\theta_d$) is $\theta_h$.

If the phase detector 11 is a mixer (multiplier) circuit, then $$V_d = k_d \cos \theta_h,$$

and $$k_d V_{inp} V_{op}$$

where $V_{inp}$ is the peak input signal, and $V_{op}$ is the peak VCO signal.

This method is to be contrasted with a phase-locked loop in which a first-order feedback loop is obtained by connecting $V_d$ directly to the VCO frequency control ($V_f$). Phase detectors can have large harmonic signals that degrade the performance of a phase locked loop unless they are filtered. Filters must be carefully designed to avoid an unstable feedback loop. The new invention has superior behavior to a phase locked loop and gives a markedly cleaner output signal, $V_f$.

Here, the VCO phase and frequency do not appear directly in the phase detector output. Instead, the loop relies on the frequency dependence of the cantilever phase. Assuming a second order cantilever, the cantilever transfer function H(f) is $$H(f) = \frac{1}{1 + \frac{jf}{Qf_n} - \left(\frac{f}{f_n}\right)^2},$$

where j is the square root of −1. The cantilever phase is $$\theta_h = -\text{ArcCos}\left[|H(f)|\left\{1 - \left(\frac{f}{f_n}\right)^2\right\}\right]$$

where the transfer function magnitude is $$|H(f)| = \frac{1}{\sqrt{\left(\frac{f}{Qf_n}\right)^2 + \left[1 - \left(\frac{f}{f_n}\right)^2\right]^2}}.$$

For frequencies close to $f_n$, $$\theta_h \approx -\frac{2Q(f - f_n)}{f_n} - \frac{\pi}{2}.$$

If the set point is −π/2 then the error signal will be zero when f=$f_n$.

The integrator 13 has a transfer function F(f)=$A_o$/j2πf, which allows it to follow the phase detector output having a magnitude, $V_d$, and a phase $\theta_d$, so that the phase will be forced to match a set-point phase. The set point is adjusted and summed with the output of the filter 12 at the summing junction 15. An alternative to adjusting a set point to adjust the desired phase, is to insert a phase delay ($\theta_{delay}$) into the cantilever signal path. If the set point is zero, then the detected phase will be $\theta_d = \theta_h + \theta_{delay}$.

This is especially useful if the desired $\theta_h$ is 0 or π. Since most phase detectors have zero output for $\theta_h = \pm\pi/2$, setting $\theta_{delay} = \pm\pi/2$ will result in a zero phase-detector output at the $\theta_h = 0$ or π. The integrator circuit 13 will ramp up or down to adjust $f_o$ so that the desired phase is obtained.

Figure 3:
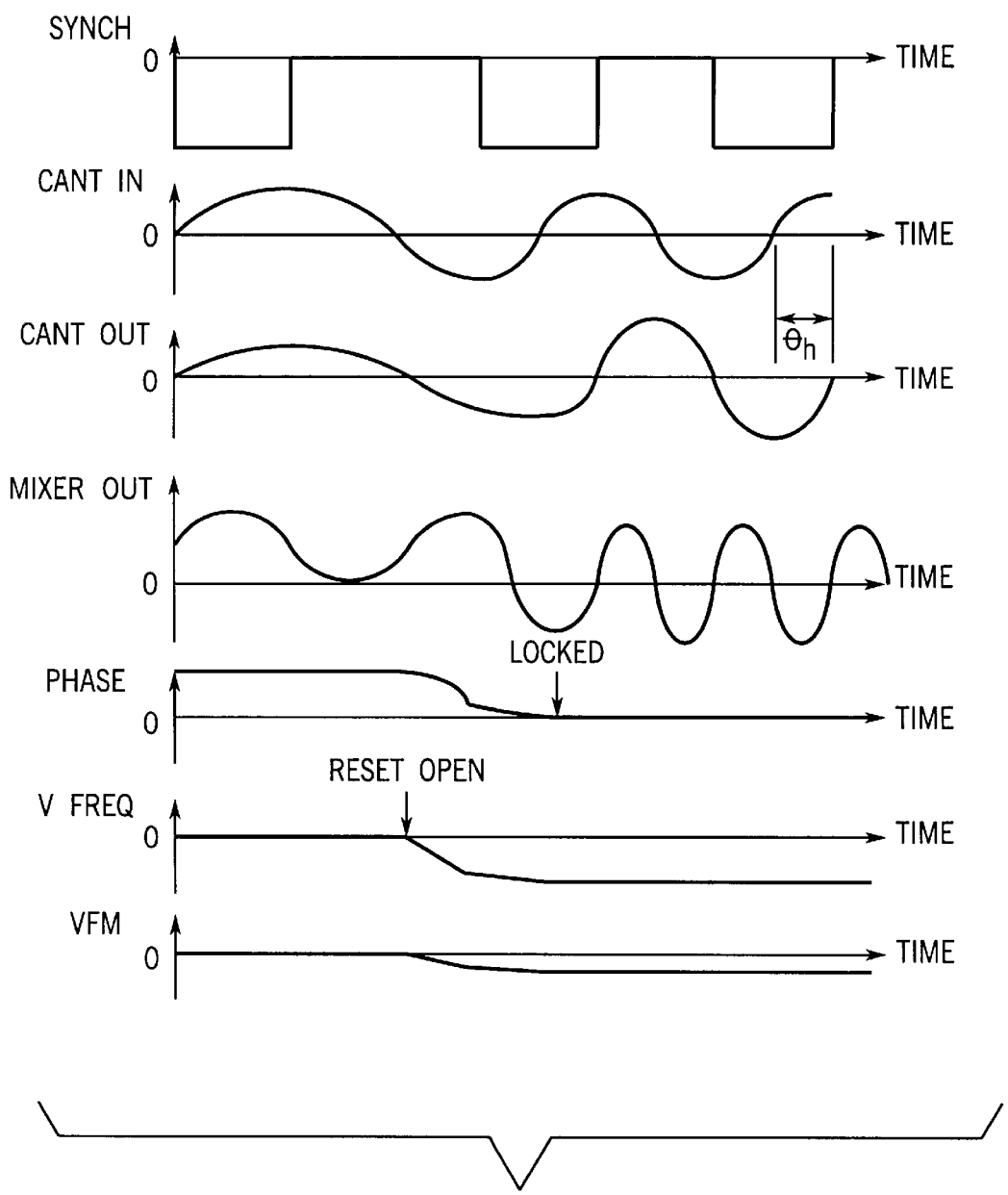
FIG. 3 is a timing diagram showing a plurality of signals produced by the apparatus of FIGS. 1 and 2.

Unlike a phase locked loop, where the frequency bounces around until phase lock is obtained, the PHASE signal (FIG. 3) of the present invention is quickly damped and locked to zero with little or no overshoot and no frequency bounce. Also, the integrator 13 produces a frequency control signal, $V_f$, that is much smoother than that of a phase-locked loop. Moreover, frequency compensation is simpler since a quiet frequency control is obtained without the need for additional filtering.

A specific embodiment of a resonance frequency change detection circuit is illustrated in FIG. 2. A micro-cantilevered spring element 10 is shown supported on a fulcrum 16 and is fabricated of quartz or silicon, for example, and is of very small size and monolithic in structure. A piezoelectric crystal transducer 17 is attached to one end of the treated micro-cantilevered spring element 10. A laser beam 18 is emitted by laser diode 19, and is reflected from a surface of micro-cantilevered spring element 10. The sweep of such reflection 20 is detected by an optical transducer 22 which includes photo diodes. As the reflected beam 20 sweeps back and forth across the transducer 22, it produces a repetitive signal (CANT OUT) (FIG. 3) with an amplitude proportional to the displacement and with a frequency equal to the oscillation frequency of the micro-cantilevered spring Element 10. The optical transducer 22 can be a displacement detector having a first cell 23 and a second cell 24, commonly known as a bicell, in which signals are processed to produce a resultant CANT OUT signal.

The phase difference between the CANT IN signal and the CANT OUT signal (FIG. 3) is related to changes in the oscillating mass and spring constant of micro-cantilevered spring element 10 due to an accumulation of target chemicals or compounds on the micro-cantilevered spring element 10. Such accumulations are induced by the chemically selective treated regions of microcantilever 12. These chemically selective treated regions provide sensitivity and selectivity. Selectivity will depend on how uniquely a specific vapor or class of vapors interact with the treated regions.

The CANT OUT signal (FIG. 3) is transmitted to an "X1" input on a mixer circuit 30 (FIG. 2), which is preferably an AD734 circuit available from Analog Devices. The VCO OUT signal is received at a "Y1" input (FIG. 2), and from these two inputs the circuit 30 performs phase detection, and provides a MIXER OUT signal from the connected outputs "Z1" and "W".

The MIXER OUT signal (FIG. 3) contains the phase information, but to convert this to a PHASE difference signal, the MIXER OUT signal is transmitted through resistor R2 to a first integrator circuit configured as the low pass filter 12. A suitable operational amplifier 31, such as an LM347 or LMC6082 available from National Semiconductor, has resistor R1 and capacitors C5 and C4 configured for this operation. Capacitors C1 and C2 are power supply bypass capacitors. A set point reference voltage is provided by potentiometer R3, R8, and is applied to a summing junction at the input of circuit 32. This allows a predetermined phase error reference to be summed with the phase error to obtain a null point, where $V_e \angle \theta_e = 0$.

Because phase detector circuit 11 has a large double-frequency component that would cause malfunction of the nonlinear integrator 13, the filter circuit 12 is a 200-Hz second-order Butterworth filter, which is used to attenuate this component by more than two orders of magnitude (>52 dB). The system in FIG. 2 has a small signal noise bandwidth of 2.7 Hz for a 2-kHz cantilever having a Q of 10 and 7 $V_{rms}$ at the mixer input. This low bandwidth is used to reduce frequency noise by over an order of magnitude (>20 dB). The bandwidth is proportional to Q/$f_n$ for low to moderately high Q's and the mixer input signal level. Thus, the instrument automatically adjusts bandwidth to reduce changes in frequency noise and the bandwidth and is self-limiting for very high Q cantilevers.

The phase error (PHASE in FIG. 3) is an input signal to the integrator circuit 13, which includes a suitable operational amplifier 32, such as an LM347 or LMC6082 available from National Semiconductor, with biasing components configured for this operation. Alternatively, a TL072 dual operational amplifier circuit may be used for the low pass filter 12 and integrator 13. A reset switch 33 (FIG. 2) is connected across the integrator circuit 13 through resistor, R14, so that the circuit 14 can be reset and then turned on to sense and lock onto an initial cantilever frequency. This switching is represented by the "RESET OPEN" point in the graph of V FREQ in FIG. 3. The PHASE ERROR is then locked near zero a short time later.

The integrator circuit 14 is more particularly a non-linear integrator circuit for handling phase error signals of a wider range. In its simplest form the invention can be practiced with a linear integrator circuit. In the non-linear integrator 14, when the phase error magnitude is less than approximately 0.4 V, the gain is controlled by resistor R4 (FIG. 2). When the phase error magnitude is more than approximately 0.4 V, the gain is controlled by R4 and R5, which increases the gain by a factor of eleven. Diodes D1 and D2 (FIG. 2) increase the integrator gain as the phase error signal (PHASE) increases in magnitude to reduce lock time when the starting frequency is not close to the natural frequency. Diode D5 (FIG. 2) clamps the VCO input voltage (VFM) to less than 0.7 volts since the VCO input control signal (VFM) should be negative; i.e., the frequency is proportional to −VFM. Diode D3 (FIG. 2) keeps the integrator error signal near zero when the overall feedback loop is opened (e.g., the cantilever is disconnected from the input) so that recovery time is reduced when the overall feedback loop is closed.

The VCO integrated circuit package 34 (FIG. 2) is preferably an ICL8038A available from Harris Semiconductor. If the VCO frequency is directly proportional to $V_f$ (V FREQ in FIG. 3), then the frequency may be determined by measuring $V_f$. The VCO 34 also generates a synchronization pulse for each cycle which may be counted by an external frequency counter circuit (not shown) to determine frequency. The frequency counter can be connected to output 35 (FIG. 2) to monitor the SYNC output from the "SQ0" output on the VCO. The VCO circuit 34 transmits the VCO OUT signal through coupling capacitor C13, and this signal becomes the CANT IN signal to the transducer 17.

Potentiometer R11, R20 is connected to the integrator output (and to the VFM input to VCO circuit 34) to provide an offset voltage that adjusts the starting frequency signal, and therefore allows for faster lock times in determining the natural frequency of oscillation of the cantilever. With spring elements having multiple natural frequencies, one of the natural frequencies may be selected by adjusting the starting frequency close to a selected natural frequency.

This has been a description of a preferred embodiment of the invention. Various modifications will be apparent to those of ordinary skill in the art and these are intended to be practiced without departing from the scope of the invention. For example, the VCO current could be controlled by a current signal as well as a voltage signal without departing from the scope of the invention. Therefore, reference is made to the claims which follow for defining the legal scope of the invention.

I claim:

1. A method for measuring a natural resonant frequency of movement of a spring element, the method comprising:

causing vibratory movement of the spring element;

applying an electrical input signal of adjustable frequency and variable phase from a voltage controlled oscillator to a transducer coupled to the spring element;

converting movement of the spring element to an electrical output signal;

detecting a phase difference between the electrical input signal and the electrical output signal, wherein said phase difference represents an oscillation frequency of the spring element due to accumulation of chemical substances on a surface thereof;

integrating the phase difference to provide an input to the voltage controlled oscillator; and wherein the voltage controlled oscillator adjusts the frequency of the electrical input signal until the phase difference which is obtained corresponds to the natural resonant frequency of vibratory movement of the spring element.

2. The method of claim 1, wherein the spring element is a micro-cantilevered element.

3. The method of claim 1, wherein said transducer is a piezoelectric element for converting the electrical input signal to the vibratory movement.

4. The method of claim 1, further comprising:

producing a control signal in response to said phase difference;

adjusting the frequency of the electrical input signal in response to the control signal;

transmitting the electrical input signal directly to a phase detector circuit that also receives the electrical output signal in response to movement of the spring element; and said phase detector circuit producing a phase difference output signal in which the phase difference is due to the vibratory movement of the spring element.

5. The method of claim 4, further comprising the steps of:

comparing the phase difference signal to a preset phase to generate a phase error signal; and integrating the phase error signal to produce the control signal.

6. The method of claim 5, further comprising filtering the phase difference signal before comparing the phase difference signal to a preset phase to generate a phase error signal.

7. An apparatus for measuring a natural frequency of movement of a spring element, the apparatus comprising:

a first transducer coupled to the spring element;

means for causing vibratory movement of the spring element;

a second transducer for converting movement of the spring element to an electrical output signal;

a phase detector for detecting a phase difference between the electrical input signal and the electrical output signal, wherein said phase difference represents an oscillation frequency of the spring element due to accumulation of chemical substances on a surface thereof; and a voltage controlled oscillator for adjusting the frequency of the electrical input signal until a phase difference is obtained that corresponds to a natural oscillating frequency for vibratory movement of the spring element due to accumulation of chemical substances on a surface thereof;

an integrator for integrating the phase difference to provide the input to the voltage controlled oscillator.

8. The apparatus of claim 7, wherein the spring element is a micro-cantilevered element.

9. The apparatus of claim 7, wherein said first transducer is a piezoelectric element for converting the electrical input signal to the vibratory movement.

10. The apparatus of claim 7, wherein the phase detector produces a phase difference signal; and further comprising a low pass filter for receiving and filtering the phase difference signal.

11. The apparatus of claim 7, wherein the electrical input signal is applied to the first transducer and is also applied to a first input of the phase detector, and wherein the electrical output signal from the second transducer is applied to a second input of the phase detector.

* * * * *